United States Patent
Cleveland et al.

(10) Patent No.: US 11,638,697 B2
(45) Date of Patent: May 2, 2023

(54) SOLID ORAL SULFATE SALT FORMULATIONS FOR CLEANING A COLON AND METHODS OF USING SAME

(71) Applicant: Braintree Laboratories, Inc., Braintree, MA (US)

(72) Inventors: Mark vB Cleveland, Norwell, MA (US); Edmund V. Dennett, Jr., Walpole, MA (US); Russell W Pelham, Duxbury, MA (US)

(73) Assignee: Braintree Laboratories, Inc., Braintree, MA (US)

(*) Notice: Subject to any disclaimer, the term of this patent is extended or adjusted under 35 U.S.C. 154(b) by 0 days.

(21) Appl. No.: 17/340,973

(22) Filed: Jun. 7, 2021

(65) Prior Publication Data
US 2021/0290546 A1    Sep. 23, 2021

Related U.S. Application Data

(63) Continuation of application No. 16/207,800, filed on Dec. 3, 2018, now Pat. No. 11,033,498, which is a continuation of application No. 15/669,749, filed on Aug. 4, 2017, now Pat. No. 10,143,656.

(51) Int. Cl.
| | |
|---|---|
| A61K 9/20 | (2006.01) |
| A61K 33/14 | (2006.01) |
| A61K 33/04 | (2006.01) |
| A61K 9/28 | (2006.01) |

(52) U.S. Cl.
CPC ............. *A61K 9/20* (2013.01); *A61K 9/2853* (2013.01); *A61K 33/04* (2013.01); *A61K 33/14* (2013.01)

(58) Field of Classification Search
None
See application file for complete search history.

(56) References Cited

U.S. PATENT DOCUMENTS

| | | |
|---|---|---|
| 3,873,694 A | 3/1975 | Kanig |
| 4,975,286 A | 12/1990 | Hechter |
| 5,124,144 A | 6/1992 | Giorgetti et al. |
| 5,616,346 A | 4/1997 | Aronchick |
| 6,162,464 A | 12/2000 | Jacob et al. |
| 6,235,745 B1 | 5/2001 | Megens |
| 6,946,149 B2 | 9/2005 | Cleveland |
| 7,169,381 B2 | 1/2007 | Barras et al. |
| 7,332,184 B2 | 2/2008 | Vanner et al. |
| 7,658,914 B2 | 2/2010 | Barras et al. |
| 7,687,075 B2 | 3/2010 | Skiendzielewski et al. |
| 7,998,510 B2 | 8/2011 | Caswell |
| 8,425,944 B2 | 4/2013 | Caswell |
| 8,507,009 B2 | 8/2013 | Skiendzielewski et al. |
| 8,778,306 B2 | 7/2014 | Bachwich |
| 9,238,075 B2 | 1/2016 | Gorelick et al. |
| 9,433,660 B2 | 9/2016 | Gorelick et al. |
| 9,919,007 B2 | 3/2018 | Dennett, Jr. et al. |
| 10,143,656 B1 * | 12/2018 | Cleveland ............... A61K 33/04 |
| 11,033,498 B2 * | 6/2021 | Cleveland ............ A61K 9/2853 |
| 2005/0271749 A1 | 12/2005 | Borody et al. |
| 2009/0258090 A1 | 10/2009 | Cleveland |
| 2011/0189091 A1 * | 8/2011 | Bachwich ................. A61P 1/10 |
| | | 424/9.1 |
| 2012/0265011 A1 | 10/2012 | Pelham |
| 2013/0189377 A1 | 7/2013 | Cockett et al. |
| 2013/0296314 A1 * | 11/2013 | Borody ............... A61K 31/4412 |
| | | 514/230.5 |
| 2014/0087007 A1 | 3/2014 | Cleveland et al. |

FOREIGN PATENT DOCUMENTS

| | | |
|---|---|---|
| CN | 101087593 | 12/2007 |
| WO | 03092589 | 11/2003 |
| WO | 2009108730 | 9/2009 |
| WO | 2012013928 | 2/2012 |
| WO | 2013059881 | 5/2013 |
| WO | 2014144407 | 9/2014 |

OTHER PUBLICATIONS

Hamed Laroui et al. Dextran Sodium Sulfates (DSS) Induces Colitis in Mice by forming Nano-Lipocomplexes with Medium-Chain-Length Fatty Acids in the Colon PLoS One, 7(3):e32084 (2012).
Russel W. Pelham, et al. Safety of Oral Sulfates in Rats and Dogs Contrasted with Phosphates-Induced Nephropathy in Rats. International J of Toxicology 28(2):99-112 (2009).
Chavous, 2013, Chart, Description—CN10187593 & U.S. Pat. No. 3,873,694.
Sodium Sulphate, Potassium Sulfate and Magnesium Sulfate Oral Solutions; PEG-3350, Sodium Chloride, Sodiym Bicarbonate and Potassium Chloride for Oral Solution (SUCLEAR), National Drug Monograph, Nov. 2014.
Chavous 2013, Chart, Description—WO03/092589 and U.S. Pat. No. 3,873,694.
Fleet Corporation, Fleet PhosphoSoda Label, 1999.
Robert H. Hawes. A consensus document on Bowel Preparation Before Colonoscopy: Prepared by a Task Force From the American Society of Colon and Rectal Surgeons (ASCRS), the American Society for Gastrointestinal Endoscopy ASGE), and the Society of American Gastrointestinal and Endoscopic Surgeons (SAGES). Gastrointestinal Endoscopy 63(7):894-909 (2006).
European Search Report EP15840422.8, dated Apr. 4, 2018.
Braintree Laboratories, SUPREP, Aug. 2010.

* cited by examiner

*Primary Examiner* — Aradhana Sasan

(57) ABSTRACT

Disclosed herein are solid oral dosage formulations comprising sodium sulfate, magnesium sulfate, and potassium chloride for inducing purgation of the colon of a subject. Furthermore, the disclosed compositions and formulations are useful to cleanse the colon when administered in sufficient quantities. Methods for inducing purgation of the colon and for cleansing the colon are also disclosed.

7 Claims, No Drawings

SOLID ORAL SULFATE SALT FORMULATIONS FOR CLEANING A COLON AND METHODS OF USING SAME

This application is a continuation of application Ser. No. 16/207,800, to be issued as U.S. Pat. No. 11,033,498, filed on Dec. 3, 2018, which is a continuation of U.S. patent application Ser. No. 15/669,749, now U.S. Pat. No. 10,143,656, filed on Aug. 4, 2017, the entireties of which are incorporated herein.

FIELD

This disclosure relates generally to the field of medicine and particularly to gastrointestinal diagnostic and surgical procedures.

BACKGROUND

When performing medical or diagnostic procedures on the colon, the colon must be cleansed of fecal matter to permit adequate visualization of the intestinal mucosa. This is important prior to, for example, diagnostic procedures such as flexible sigmoidoscopy or colonoscopy, diagnostic examinations widely performed to screen patients for diseases of the colon. In addition, it is important that the intestines be cleansed thoroughly in order to obtain satisfactory radiographs of the colon.

Existing bowel preparations are generally presented in a liquid form, such as the isotonic large volume preparations GoLYTELY and NuLYTELY which are based on polyethylene glycol (PEG) as the osmotic agent, or the smaller volume preparations such as MOVIPREP (a slightly hypertonic solution also based on PEG), SUPREP (based on sulfate as the osmotic agent) and Phosphosoda (based on phosphate). The larger volume preparations require ingestion of up to 4 liters (about 1 gallon) of solution (Davis et al. 1980; Fordtran et al. 1990). While recognized as the safest products, these large-volume preparations produce patient discomfort often resulting in poor compliance due to the large volume of salty tasting solution that must be consumed. An early innovation attempting to solve this problem was the development of a split dose hypertonic solution. The product, sold under the name Phosphosoda, was recognized to produce excellent bowel cleansing and required the ingestion of only a small volume of solution (Vanner et al. 1990). The product was also made into tablets, sold under the name Osmoprep (Aronchick et al. 2000). Although these products enjoyed improved patient tolerance, because they were formulated using salts of phosphate, they became associated with risk of renal failure due to renal calcium phosphate deposition (resulting from absorption of the phosphate anion) eventually prompting the FDA to issue a warning concerning their use (USFDA Alert 2008). A further innovation was the development of an alternative hypertonic preparation based on a unique combination of three sulfate salts (Cleveland/Fordtran Patent). Approved by FDA in 2010, SUPREP combined sulfate salts of sodium, potassium and magnesium in such a manner as to balance or compensate for electrolyte losses and gains resulting from the copious diarrhea induced by the osmotically active sulfate anion without risk of renal calcification (Patel et al. 2009).

Development studies had shown that all three sulfate salts were required in the liquid formulation and that the SUPREP formulation produced cleansing diarrheal stool output similar to Phosphosoda (about 2400 ml: Cleveland/Fordtran Patent, Patel et al 2009). Generally, the three sulfate salts were balanced to provide the proper cleansing required for diagnostic tests and to reduce the likelihood of electrolyte shifts.

The art has disclosed the use of non-aqueous formulations of sulfate and phosphate salts. However, these formulations have had drawbacks including insufficient cleansing and potential safety issues. Furthermore, sulfate salt formulations require large amounts of tablets to cleanse the colon—a typically undesirable requirement for most patients—and are very unpalatable due to a highly salty taste (see, e.g., U.S. Pat. No. 6,103,268). Thus, the known non-aqueous formulations have undesired characteristics that lead to unsatisfactory results in a substantial population of patients.

As disclosed herein, the inventors have discovered that sulfate salt formulations require only two sulfate salts (sodium and magnesium sulfate) relying upon the osmotic activity of sulfate anion which is poorly absorbed. In addition, the inventors have discovered that formulations lacking potassium sulfate can be formulated to prevent electrolyte gains or losses from the resulting cleansing diarrhea following ingestion of the tablets.

SUMMARY

Disclosed herein are compositions (alternatively, "formulations") that are effective and safe to cleanse the colon of a subject. The formulations are effective to induce purgation of the colon and are further safe and effective to cleanse the colon. As used herein, the term "purgation" means evacuation of a copious amount of stool from the bowels after oral administration of a composition. Furthermore, disclosed herein are methods for cleansing of the colon of a subject, as well as methods for cleansing the colon. Also, disclosed herein are methods of inducing purgation of the colon. The disclosed compositions also do not cause clinically significant electrolyte shifts and are thus useful for preparation of patients for diagnostic and surgical procedures. Such diagnostic and surgical procedures include, but are not limited to, colonoscopy, sigmoidoscopy, radiographic examination, bowel surgery, colon resection, and other colorectal procedures. Furthermore, the present compositions, formulations, and methods allow for treatment of conditions such as fecal retention, constipation, and hard stools by providing a formulation that can be used as a laxative when administered in lower doses than used for colon cleansing.

Aspects of the compositions disclosed herein include a solid oral dosage formulation for cleansing a colon of a subject. As used herein, the term "a" means one or more unless specifically defined otherwise. In certain embodiments, the formulation comprises from about 30.0 grams to about 40.0 grams of sodium sulfate, from about 4.0 grams to about 8.0 grams of magnesium sulfate, and from about 3.0 grams to about 5.0 grams of potassium chloride. In specific embodiments, the formulation comprises from about 34.0 grams to about 36.0 grams of sodium sulfate, about 5.0 grams to about 8.0 grams of magnesium sulfate, and about 3.5 grams to about 4.5 grams of potassium chloride. As used herein, the term "about" means within +/−10% of the recited value. For instance, about 2.0 would cover from 1.8 to 2.2. In more specific embodiments, the formulation comprises either about 34.6 grams or about 35.5 grams of sodium sulfate, either about 5.4 grams or about 7.8 grams of magnesium sulfate, and either about 3.7 grams or about 4.5 grams of potassium chloride. In some embodiments, the formulations comprise about 0.1 grams to about 1.0 grams of sodium caprylate. In other embodiments, the formulations comprise about 0.8 grams of sodium caprylate. In yet other embodiments, the formulations comprise about 0.168 grams of sodium caprylate.

In some embodiments, the sodium sulfate, magnesium sulfate, and potassium chloride are compressed into about 14 to about 42 tablets. In other embodiments, the disclosed formulation is compressed into about 18 to about 38 tablets. In still other embodiments, the formulation is compressed into about 20 to about 36 tablets, about 22 to about 34 tablets, about 24 to about 32 tablets, or about 26 to about 30 tablets. In particular embodiments, the formulation is compressed into about 24 tablets. In other particular embodiments, the formulation is compressed into about 28 tablets. In other embodiments, the formulation is divided into two or more doses. In still other embodiments, each dose comprises about 7 to about 21 tablets. In yet more embodiments, each dose comprises about 12 tablets or about 14 tablets.

In particular embodiments, the formulation delivers from about 450 millimoles to about 550 millimoles of sodium, from about 40 millimoles to about 70 millimoles of magnesium, from about 50 millimoles to about 60 millimoles of potassium, from about 50 millimoles to about 60 millimoles of chloride, and from about 250 millimoles to about 350 millimoles of sulfate. In certain embodiments, the formulation delivers either about 493 millimoles or about 500 millimoles of sodium, either about 45 millimoles or about 65 millimoles of magnesium, either about 50 millimoles or about 60 millimoles of potassium, either about 50 millimoles or about 60 millimoles of chloride, and either about 295 millimoles or about 309 millimoles of sulfate.

In other embodiments, the formulation consists of about 35.5 grams or about 34.6 grams of sodium sulfate, about 5.4 grams or about 7.8 grams of magnesium sulfate, and about 3.7 grams or about 4.5 grams of potassium chloride. In more particular embodiments, the formulations are compressed into about 24 tablets.

In still more embodiments, the formulation does not cause clinically significant electrolyte shifts in the subject.

Additional aspects comprise a solid oral formulation for inducing purgation of a colon of a subject. In certain embodiments, the formulation comprises from about 17.0 grams to about 20.0 grams of sodium sulfate, from about 2.0 grams to about 4.0 grams of magnesium sulfate, and from about 1.5 grams to about 2.5 grams of potassium chloride. In specific embodiments, the formulation comprises at least about 17.3 grams of sodium sulfate, at least about 2.7 grams of magnesium sulfate, and at least about 1.8 grams of potassium chloride.

In certain embodiments, the formulation is compressed into tablet form. The formulation can also be compressed into capsules, caplets, and other solid dosage units that can be administered to a patient. Such dosage forms contain predetermined amounts of active ingredients, and can be prepared by methods of pharmacy well known to those skilled in the art (Remington's Pharmaceutical Sciences, 18th ed., Mack Publishing, Easton Pa. (1990)). In other embodiments, the formulation comprises about 12 tablets.

In yet other embodiments, the formulation does not cause clinically significant electrolyte shifts in the subject. In further embodiments, the formulations dissolve sufficiently to cause a purgative effect and in sufficient doses to cleanse the colon.

Further aspects include a method of cleansing a colon of a subject. The method comprises administering a solid oral formulation to the subject. In some embodiments, the solid oral dosage formulation comprises from about 30.0 grams to about 40.0 grams of sodium sulfate, from about 4.0 grams to about 8.0 grams of magnesium sulfate, and from about 3.0 grams to about 5.0 grams of potassium chloride. In specific embodiments, the formulation comprises from about 34.0 grams to about 38.0 grams of sodium sulfate, about 4.0 grams to about 8.0 grams of magnesium sulfate, and about 3.0 grams to about 5.0 grams of potassium chloride. As used herein, the term "about" means within +/−10% of the recited value. For instance, about 2.0 would cover from 1.8 to 2.2. In more specific embodiments, the formulation comprises either about 34.6 grams or about 35.5 grams of sodium sulfate, either about 5.4 grams or about 7.8 grams of magnesium sulfate, and either about 3.7 grams or about 4.5 grams of potassium chloride. In some embodiments, the formulations comprise about 0.2 grams to about 1.0 grams of sodium caprylate. In other embodiments, the formulations comprise about 0.8 grams of sodium caprylate. In some embodiments, the formulations comprise from about 1.6 grams to about 2.1 grams of polyethylene glycol. In other embodiments, the formulations comprise from about 1.0 grams to about 3.0 grams of polyethylene glycol. In particular embodiments, the polyethylene glycol is PEG-8000. The methods allow for administration of the solid oral formulation such that the formulation induces purgation of the subject's colon such that the colon is cleansed of fecal matter.

In some embodiments, the amount of bisacodyl administered to the subject is from 5.0 mg to about 15.0 mg. In other embodiments, the solid oral formulation is administered with or further comprises from about 60.0 grams to about 100 grams of PEG. For instance, the PEG can be co-administered as a solution with the solid oral formulation.

In still other embodiments, the solid oral formulation is in the form of a powder, tablet, or sachet. In still further embodiments, the formulation does not cause clinically significant electrolyte shifts in a subject. One of ordinary skill in the art will recognize that a clinically significant event must have a genuine, noticeable, and unexpected effect on the life of a subject. Mere changes in electrolyte levels outside of a given range in a single patient or small group of patients will not rise to the level of a clinically significant event. Rather, a clinically significant event is one that substantially effects the life of a subject. A clinically significant electrolyte shift can also be found when the mean electrolyte levels of a population shift outside of the normal range for the population of patients, not just in an individual patient or small group of patients within the population. Furthermore, one of ordinary skill will recognize that an event must be unexpected as well. For instance, the disclosed formulations are designed to purge the colon and such formulations would be expected to cause diarrhea, in some cases, vomiting, and dehydration. These events would not be clinically significant events due to their being expected in some individuals.

In some embodiments, the pharmaceutical tablet composition further comprises one or more soluble excipients. In other embodiments, the one or more excipients soluble in aqueous solutions are selected from the group consisting of binders, lubricants, glidants, disintegrants, and combinations thereof. In still other embodiments, the one or more soluble excipients are selected from the group consisting of micronized polyethylene glycol, sodium dodecyl sulfate, sodium lauryl sulfate, sodium stearyl fumarate, sodium benzoate, sodium caprylate, and combinations thereof.

In some embodiments, the one or more soluble excipients are selected from the group consisting of binders, lubricants, glidants, disintegrants, and combinations thereof. In other embodiments, the one or more water soluble excipients are selected from the group consisting of polyethylene glycol, such as PEG-8000, sodium dodecyl sulfate, sodium lauryl sulfate, sodium benzoate, sodium stearyl fumarate, sodium caprylate, and combinations thereof.

In certain embodiments, the formulation is administered on the same day as a surgical procedure. In yet more embodiments, the formulation is administered the day before a surgical procedure. In other embodiments, the formulation is administered as a split dose. In particular embodiments, the formulation is provided as a half dose the day before the procedure and a half dose the day of the procedure.

DETAILED DESCRIPTION

1. Tablet Cleansing Formulations

Disclosed herein are pharmaceutical tablet formulations useful for inducing purgation of the colon and further useful for cleansing the colon. As used herein, the terms "tablet," "tablet composition," and "tablet formulation" each individually refer to a composition or formulation that contains a mixture of active pharmaceutical ingredients and/or excipients (i.e., inactive ingredients) that can be formed into a solid dosage unit by way of its designed and inherent compactability, flowability, and adherence characteristics. Exemplary formulations can be compressed consecutively and continuously, manufactured or produced, into dosage units using compression style tableting equipment.

The disclosed compositions and formulations produce dosage units that, when manufactured, exhibit consistent and acceptable physical characteristics. The dosage units must also be appropriate for ingestion by a patient and meet desirable and measurable pharmaceutical performance and quality attributes. Aspects of the compositions disclosed herein comprise sodium sulfate. In some embodiments, the sodium sulfate is selected from the group consisting of anhydrous sodium sulfate and sodium sulfate hydrates such as sodium sulfate decahydrate.

As used in certain aspects disclosed herein, sodium sulfate allows for purging of the colon of a patient to achieve cleansing. In particular uses, sufficient sodium sulfate to participate in cleansing the colon is administered over a period of time (e.g., six or more hours, 12 or more hours, and up to 24 hours). Without being held to any particular theory, the sulfate salts are poorly absorbable and cause water to flow into the intestine when provided in the intestine in sufficient quantities. Poorly-absorbable salts exhibit limited uptake from the intestine and that the salts remaining in the intestine cause water to flow into the intestines. Accordingly, the pharmaceutical tablet formulations disclosed herein can be administered with water to induce purgation of the colon of a subject (e.g., patient) and such compositions can be used to cleanse the colon when administered in sufficient quantities. A further advantage of the presently disclosed compositions is that such compositions do not cause clinically significant electrolyte shifts when administered in sufficient quantities to induce purgation of the colon and balanced with other salts as disclosed herein. In some embodiments, the electrolyte shifts that the disclosed formulations avoid are shifts in sodium, magnesium, potassium, and chloride. The disclosed formulations avoid such shifts by providing sufficient amounts of sodium, magnesium, and potassium cations to avoid shifting the levels of these cations in a subject taking the compositions.

The formulations disclosed herein can be administered as 20 to 30 tablets to cleanse the colon, and some embodiments, administered as about 24 tablets and about 28 tablets. However, one of ordinary skill in the art will recognize from this disclosure that the formulations can be administered as about 14 to about 42 tablets, about 18 to about 38 tablets, about 20 to about 36 tablets, about 22 to about 34 tablets, about 24 to about 32 tablets, or about 26 to about 30 tablets. Each tablet can comprise from about 0.6 grams of sodium sulfate to about 3.0 grams of sodium sulfate. When a subject (e.g., a patient) is administered a cleansing dose of the formulations, the total amount of sodium sulfate is from about 25.0 grams to about 40.0 grams. In particular embodiments, the total amount of sodium sulfate is about 35.0 grams. In more particular embodiments, the sodium sulfate amounts are either 35.5 grams or about 34.6 grams. Subjects administered sodium sulfate, a cleansing dose of the formulations can deliver from about 490 millimoles to about 505 millimoles of sodium and from about 290 millimoles to about 310 millimoles of sulfate.

It should be noted that the cleansing dose can be administered in two or more administrations. In certain embodiments, the cleansing dose is administered in two doses to a subject over a period of at least six hours. The cleansing dose can also be administered in two doses over a period of at least eight hours, at least ten hours, at least twelve, or up to 24 hours. The cleansing dose can also be administered in three or more doses over a period of at least six hours, at least eight hours, at least ten hours, at least twelve, or up to 24 hours.

Aspects of the pharmaceutical tablet compositions disclosed herein sodium sulfate can comprise at least 70% (w/w) of the tablet composition. In some embodiments, the sodium sulfate comprises at least 60% (w/w) of the tablet composition. In other embodiments, the sodium sulfate comprises at least 50% (w/w) of the tablet composition. In particular embodiments, the pharmaceutical tablet compositions comprise from about 65% to about 75% sodium sulfate. In some embodiments, the pharmaceutical tablet compositions comprise at least about 70% sodium sulfate.

As described herein, the formulation comprising sodium sulfate comprises an effective amount of magnesium sulfate. It should be noted that both magnesium and sulfate contribute to purgation that allow the formulations to help cleanse the colon of a subject. In certain embodiments relating to cleansing the colon, the disclosed formulations can be administered such that the subject receives from about 4.0 grams to about 8.0 grams of magnesium sulfate. In particular embodiments, the plurality of tablets comprise from about 5.0 grams to about 8.0 grams of magnesium sulfate. In more particular embodiments, the formulations comprise either about 5.4 grams or about 7.8 grams of magnesium sulfate.

As disclosed herein, the formulations comprise sufficient magnesium sulfate (e.g., magnesium sulfate tribasic anhydrous) to induce purgation of the colon. Magnesium is poorly absorbed by the intestines of a subject and contributes to the osmotic diarrheal action of the tablets. When the formulations are administered to subjects with the amounts of magnesium sulfate and sodium sulfate disclosed herein, the formulations will induce purgation of the colon and when administered in sufficient amounts will lead to cleansing of the colon. For instance, when the tablets are administered over a period of up to 24 hours, the subject will have sufficient diarrhea to cleanse the colon of stool.

Aspects of the disclosed formulations also include potassium chloride. The amount of potassium chloride in the formulations can be from about from about 2.0 grams to about 5.0 grams. In particular embodiments, the formulations comprise from about 3.5 grams to about 5.0 grams of potassium chloride. In more particular embodiments, the formulations comprise either about 3.7 grams or about 4.5 grams of potassium sulfate.

As noted above, the formulations can be administered in tablet form in numbers from about 24 tablets, about 28 tablets, about 14 to about 42 tablets, about 18 to about 38 tablets, about 20 to about 36 tablets, about 22 to about 34 tablets, about 24 to about 32 tablets, or about 26 to about 30 tablets. It should be recognized that each tablet therefore comprises a subdivided amount of magnesium sulfate from the formulation total. In other words, if the formulation is divided into 24 tablets, each tablet comprises from about 1.04 grams to about 1.66 grams of sodium sulfate, from about 0.16 grams to about 0.333 grams of magnesium sulfate, and from about 0.08 grams to about 0.20 grams of potassium chloride.

As noted herein, the disclosed formulations can be tablets that are combinations of sodium sulfate, magnesium sulfate, and potassium chloride. The combination of salts and amounts of each salt have been developed to avoid the clinically significant electrolyte shifts found with the use of other solid and hypertonic formulations. This balance of salts allows for inducing of osmotic diarrhea (i.e., purgation) while reducing the clinically significant gains or losses of electrolytes (i.e., shifts of electrolytes) during the process of purgation.

The pharmaceutical tablet formulations can further comprise one or more excipients. The one or more excipients (e.g., soluble) are selected from the group consisting of binders, lubricants, glidants, disintegrants, and combinations thereof. Exemplary excipients include binders such as copolyvidone, gelatin, hydroxypropyl cellulose, hydroxypropyl methylcellulose, hypromellose, lactose anhydrous, povidone, and polyethylene oxide. Other exemplary excipients include emulsifying agents such as hydroxypropyl cellulose, polaxamer 407, and sodium lauryl sulfate. Additional exemplary excipients include soluble lubricants. Water-insoluble lubricants such as magnesium stearate, stearic acid, hydrogenated vegetable oil, and glyceryl palmitostearate leave insoluble residues in the colon that interfere with diagnostic visualization of the colon. Accordingly, the disclosed compositions utilize water-soluble lubricants such as polyethylene glycol, polaxamer 407, sodium lauryl sulfate, sodium benzoate, sodium dodecyl sulfate, sodium caprylate, and sodium stearyl sulfate. Further exemplary excipients include disintegrants such as citric acid, croscarmellose sodium, and povidone. In certain embodiments, the tablet formulations disclosed herein comprise sodium caprylate in an amount from about 0.1 grams to about 1.0 grams. In particular embodiments, the tablet formulations comprise about 0.442 grams of sodium caprylate or 0.84 grams of sodium caprylate, such as embodiments in which the formulations comprise 24 tablets of compressed sodium sulfate, magnesium sulfate, and potassium chloride.

In some embodiments, the pharmaceutical tablet formulations comprise only a very minimal amount of water-soluble excipients. The benefit being that these tablets will dissolve clearly leaving no insoluble residue in the gastrointestinal tract. In particular embodiments, the one or more soluble excipients are selected from the group consisting of polyethylene glycol, sodium dodecyl sulfate, sodium lauryl sulfate, sodium stearyl fumarate, sodium benzoate, sodium caprylate, and combinations thereof. In certain embodiments, the pharmaceutical tablet compositions comprise less than or equal to 5% (w/w) excipients in the total tablet compositions. In other embodiments, the pharmaceutical tablet compositions comprise less than or equal to 10% (w/w) excipients and alternatively less than or equal to 5% (w/w) excipients in the total tablet compositions.

Additional aspects of the disclosed formulations include the addition of other agents to assist in the cleansing of the colon of a subject. Such additional agents can be included in the tablet formulations comprising sodium sulfate, magnesium sulfate, and potassium chloride. Alternatively, the additional agents can be separate tablets or reconstituted solutions that are provided with the disclosed tablet formulations. Examples of additional agents include, but are not limited to, bisacodyl, picosulfate, and polyethylene glycol ("PEG"). In some embodiments, each tablet formulation comprises from about 1.0 grams of PEG to about 5.0 grams of PEG. In some embodiments, each tablet formulation comprises from about 1.0 grams to about 3.0 grams of PEG. In other embodiments, each tablet formulation comprises from about 1.6 grams to about 2.1 grams of PEG. In particular embodiments, the formulations comprise about 2.08 grams of PEG. In more particular embodiments, the PEG is PEG-8000 in the tablet formulation or PEG-3350 in the reconstituted solution.

In particular embodiments, the formulations comprise bisacodyl, which is a well-known stimulant laxative (Stiens et al. (1998) *Spinal Cord.* 36(11): 777-781). When bisacodyl is used with the disclosed formulations, the cleansing dose of the disclosed formulations can be decreased by one-third or one-half of the dose disclosed herein for cleansing.

In particular embodiments, the tablet formulations are administered along with a solution comprising PEG. In certain embodiments, the PEG solution is reconstituted from bulk powder PEG diluted in water. For instance, a subject can be administered from about 4 to 10 tablets of the formulation to induce purgation. The subject is also administered a reconstituted solution of PEG, where the PEG in an amount from about 50.0 grams to about 150 grams is reconstituted in 250 ml to 500 ml of water. In some embodiments, from about 60 to about 100 grams of PEG is reconstituted in 250 ml to about 500 ml of water.

It has also been discovered that commercially available sodium sulfate can form slow dissolving crystals. Such slow dissolving crystals can prevent a pharmaceutical tablet composition from dissolving sufficiently to have the desired effect on a subject. In certain embodiments, sodium sulfate particles having a diameter of less than 150 μm are removed prior to formulating pharmaceutical tablet compositions. In particular embodiments, the pharmaceutical tablet composition is substantially free of sodium sulfate particles of less than 150 μm. In some embodiments, fines of a diameter of less than 150 μm are added back to the sodium sulfate that is substantially free of such crystals. In particular embodiments, the fines comprise 10% (w/w) of the sodium sulfate. In particular embodiments, the sodium sulfate particles in the pharmaceutical tablet compositions comprises about 90% (w/w) particles having a diameter of between about 150 μm and about 700 μm and about 10% (w/w) fines (i.e., particles having a diameter of less than 150 μm) that are added back to the sodium sulfate. It is believed that the added fines increase hardness such that there is no picking. Furthermore, the compositions do not need additional lubricants beyond the levels disclosed herein. Additionally, the presently disclosed compositions allow for a wider hardness range for the compositions and a more robust formulation.

The pharmaceutical tablet formulations can be tableted using standard production style equipment and techniques (Bogda, Michael J. Ch. 260, "Tablet Compression: Machine Theory, Design, and Process Troubleshooting" in *Encyclo-*

*pedia of Pharmaceutical Technology, Third Edition,* 2006). In other embodiments, the pharmaceutical tablet formulation is encapsulated.

The coating can also be a film that coats the tablet. Film coats are most commonly deposited on the tablets by spraying a thin uniform layer on the tablet. Polymers used in film coats include sucrose, hypromellose, hydroxyethyl cellulose, hydroxyethylmethyl cellulose, carboxymethylcellulose sodium, hydroxypropyl cellulose, polyethylene glycol, and ethylcellulose. In particular embodiments, the coating quickly dissolves without affecting disintegration and/or dissolution of the tablet composition. In further embodiments, the coating does not leave a residue that affects visualization of the colon. In certain embodiments, the tablet formulation comprises a coating that comprises Kollicoat IR and water.

It is understood that the formulations disclosed herein can dissolve in buffers, body fluids, or physiological solutions. The disclosed formulations can dissolve sufficiently to allow for purgation of the colon and in sufficient amounts, cleansing of the colon. Such formulations can also disintegrate and the determination of tablet disintegration can be accomplished using in vitro test methods provided in the United States Pharmacopoeia (see e.g., United States Pharmacopoeia, Vol. 36 <711> Dissolution, pages 307-313, applying Apparatus 2 (Paddle Apparatus)). In particular embodiments, the disclosed tablet compositions cause little or no turbidity when dissolved in solution. For instance, when dissolved in solution, the tablet compositions will generate solutions having turbidities of 0 to 15 Nephelometry Turbidity Units (NTU). In more particular embodiments, the solutions will have turbidities of about 0.1 to about 10 NTU or 0.5 to 5 NTU. In even more particular embodiments, the solutions will have turbidities of about 0.1 to about 20 NTU.

2. Purgative Formulations

In particular embodiments, the formulations are administered in an amount sufficient to induce purgation, the "purgative dose." In certain embodiments, the purgative formulations comprise a plurality of tablets such as the pharmaceutical tablet compositions disclosed herein. The plurality of tablets comprise an effective amount of sodium sulfate, magnesium sulfate, and potassium chloride to induce purgation of the colon of a subject.

In certain embodiments, the purgative formulations are a plurality of tablets (such as the pharmaceutical tablet formulations disclosed herein). In particular embodiments, the purgative formulation comprises an effective amount of sodium sulfate, magnesium sulfate, and potassium chloride to induce purgation of the colon. In some embodiments, the effective amount of sodium sulfate comprises at least 60% (w/w) of the total weight of the formulation and can be up to 80% (w/w) of the total weight of the formulation. The effective amount of sodium sulfate in combination with magnesium sulfate should be sufficient to induce purgation of the colon. The avoidance of clinically significant electrolyte shifts can be accomplished by the proper balance of potassium chloride, magnesium sulfate, and sodium sulfate. Such balancing of cations to avoid clinically significant electrolyte shifts has been disclosed in U.S. Pat. No. 6,946,149, the contents of which are incorporated herein by reference.

In more particular embodiments, the plurality of tablets comprises about 7 to about 21 tablets. In particular embodiments, the plurality of tablets comprises about 8 to about 14 tablets. In some embodiments, the plurality of tablets comprises 12 tablets. In some embodiments, the formulations are administered in amounts that purge the colon of a subject. The pharmaceutical tablet compositions disclosed herein comprise an effective amount of sodium sulfate and magnesium sulfate to induce purgation of the colon.

When the formulations are administered to induce purgation of the colon, the formulations comprise from about 8.0 grams to about 25.0 grams of sodium sulfate. In specific embodiments, the formulation comprises at least about 11.0 grams to at least about 20.0 grams of sodium sulfate when administered to induce purgation. In more specific embodiments, the formulation comprises from about 17.0 grams to about 17.7 grams when administered to induce purgation. The purgative dose can be administered in an amount of about 9 to about 11, about 8 to about 12, or about 5 to about 15 tablets.

When the formulations are administered as a purgative dose, the subject receives from about 1.0 grams to about 6.0 grams of magnesium sulfate. In specific embodiments, the formulation comprises at least about 2.0 grams to at least about 4.0 grams of magnesium sulfate when administered to induce purgation of the colon. In more specific embodiments, the formulation comprises from about 2.7 grams to about 3.9 grams of magnesium sulfate when administered to induce purgation of the colon. As disclosed above, the purgative dose can be administered in an amount of about 9 to about 11, about 8 to about 12, or about 5 to about 15 tablets.

As noted herein, the formulations can be administered as a purgative dose of about 9 to about 11, about 8 to about 12, or about 5 to about 15 tablets. When administered as a purgative dose, the subject is administered from about 1.0 grams to about 4.0 grams of potassium chloride. In specific embodiments, the formulation comprises at least about 1.6 grams to at least about 2.5 grams of potassium chloride when administered to induce purgation of the colon. In more specific embodiments, the formulation comprises from about 1.8 grams to about 2.3 grams of potassium chloride when administered to induce purgation of the colon.

In particular embodiments, the formulation delivers at least about 200 millimoles to at least about 300 millimoles of sodium, at least about 20 millimoles to at least about 40 millimoles of magnesium, at least about 20 millimoles to at least about 40 millimoles of potassium, at least about 20 millimoles to at least about 40 millimoles of chloride, and at least about 100 millimoles to at least about 200 millimoles of sulfate to the subject when administered as a purgative dose.

As disclosed herein, the total dose to cleanse the colon can be administered in a split-dose with one dose the day before a diagnostic or surgical procedure and a second dose on the day of the procedure, a split dose the day before the procedure, a split dose on the day of the procedure, or as a single dose given the day before or the day of the procedure. During the cleansing protocol, each dose would cause a purgation in the subject.

3. Methods of Administering Purgative Formulations and Pharmaceutical Tablet Compositions Disclosed herein are methods of administering the purgative formulations and pharmaceutical tablet compositions. Aspects of the disclosed methods comprise administering to the subject a purgative formulation comprising a plurality of pharmaceutical tablet compositions. In certain embodiments, the purgative formulation comprises an effective amount of at least one sulfate salt.

In particular embodiments, the purgative formulations are administered in an amount effective to induce purgation of the colon. When administered to a subject, the purgative formulations provide a dose of sulfate and magnesium salts to the subject effective to purge the colon. In still other embodiments, the purgative formulation is provided to the subject such that the dose of sulfate and magnesium salts effectively cleanses the colon.

The methods disclosed herein further comprise orally administering as small of a quantity of tablets as needed to a patient. In certain embodiments, the plurality of tablets administered to the subject is at least 20 tablets. In some embodiments, the plurality of tablets administered to the subject is at least 30 tablets. In other embodiments, the plurality of tablets administered to the subject is 12 tablets. In particular embodiments, the plurality of tablets is administered to the subject in an amount of 24 tablets. In more particular embodiments, the plurality of tablets is 28 tablets. In yet more embodiments, the plurality of tablets administered to the subject is 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 tablets.

In some embodiments, the methods comprise administering a plurality of tablets in which each tablet in the plurality comprises only sodium sulfate, magnesium sulfate, and potassium chloride. In these embodiments, the multiplicity of tablets comprises sodium sulfate in an amount from about 10.0 grams to from about 40.0 grams of sodium sulfate depending on the desired effect (i.e., purgation, laxation, or cleansing). The plurality of tablets also comprises magnesium sulfate in an amount from about 1.0 grams to about 10.0 grams of magnesium sulfate depending on the desired effect (i.e., purgation, laxation, or cleansing). The plurality of tablets can comprise potassium chloride from about 1.0 grams to about 8.0 grams, depending on the desired effect (i.e., purgation, laxation, or cleansing).

Additionally, the disclosed formulations can be administered with a sufficient quantity of liquid to ease swallowing of the tablets and to avoid dehydration caused by the dose of sulfate salts administered to the subject. One of ordinary skill in the art would recognize that dehydration is a possible expected adverse event when taking the disclosed formulations with insufficient water. In certain embodiments, the liquid is a clear liquid, such as water. In particular embodiments, the total volume of liquid administered to the subject is from about 500 ml to about 1.0 liters. When the purgative formulation is administered to cleanse the colon, the volume of liquid administered to the subject can be adjusted to prevent dehydration (e.g., the volume of liquid can be increased up to 2.0 liters or more depending on the needs of the particular subject). In particular embodiments, the liquid consumed in two hours or less after ingesting the purgative formulation.

In certain embodiments, the plurality of tablets are split into two or more portions. For instance, the plurality of tablets is split into two portions, three portions, or four or more portions. The only limitation to the splitting of the plurality of tablets is to insure that the subjects experience a purgation. One of ordinary skill in the art will understand that when an additional stimulant laxative such as bisacodyl or picosulfate is used, the dose of the disclosed formulations necessary to induce purgation will likely be lower than the amount of the disclosed formulation necessary when not using a stimulant laxative. Notwithstanding the use of stimulant laxatives, the portions can be administered over a period of two or more hours, four or more hours, six or more hours, eight or more hours, ten or more hours, twelve or more hours, 14 or more hours, 16 or more hours, 18 or more hours, 20 or more hours, 22 or more hours, or 24 or more hours. Each portion of tablets is sufficient to induce purgation of the colon.

In some embodiments, the plurality of tablets is split into two portions. In such embodiments, the first portion is administered and allowed to induce purgation. At some point after purgation, the second portion is administered and allowed to induce purgation. As used herein, the term "allowed" means that a subject or physician does not intervene to cease the procedure. After the second purgation, the subject can undergo a diagnostic procedure such a colonoscopy. In these embodiments, the administration of the two portions is split by two or more hours, four or more hours, six or more hours, eight or more hours, ten or more hours, twelve or more hours, 14 or more hours, 16 or more hours, 18 or more hours, 20 or more hours, 22 or more hours, or 24 or more hours. In some embodiments, the first portion can be administered the evening before a diagnostic or surgical procedure such as a colonoscopy and the second portion can be administered on the day of a colonoscopy.

In yet another embodiment, the plurality of tablets is split into two or more doses and the doses are administered on the same day. When a split-dose regimen is performed on a single day, each portion of the regimen can be administered with about one hour to about ten hours between administrations of the doses such that the doses are all administered on the same day.

In particular embodiments, the method further comprises administering a volume of water to a subject after taking a portion of tablets. The volume of water is sufficient to allow the subject to consume the tablets. The subject is then instructed to drink additional water over a period of one to three hours. The volume of water is from about 500 ml to about 6.0 liters. One of ordinary skill in the art will recognize that larger or smaller volumes of water may be required depending on the age, health, or other factors present for a patient. It is typical for the subject to be instructed not to consume food or colored liquids during the course of the regimen.

In certain embodiments, the tablets are administered in a single dose of 20 to 30 tablets. For instance, the tablets can be administered in a dose of 24 tablets. In such embodiments, the tablets are provided with a sufficient quantity of water to allow the subject to consume the tablets. In particular embodiments, an additional 500 ml to 2.0 liters of water (in some embodiments, 1.0 to 1.5 liters of water) are consumed by the patient over a period of one to three hours after consuming the tablets. In this full-dose regimen, the regimen can be performed the evening before a diagnostic or surgical procedure or the day of the procedure.

4. Methods of Manufacture

Disclosed herein are methods of manufacturing the disclosed compositions. Aspects of the methods include combining one or more water soluble salts, one or more water soluble binders, and one or more water soluble lubricants. The disclosed methods include blending the one or more salts using blender such as a standard slant cone or cone blender (GEMCO, Middlesex, N.J.). Other types or classifications of blending equipment may be utilized in place of the cone style blending equipment where appropriate. In certain embodiments, the salts are added to the blender and tumbled for between about 10 and about 60 minutes.

In particular embodiments, the one or more salts, one or more binders, and one or more lubricants requires particle size reduction or modification. Such techniques are known to those of ordinary skill in the art. In particular embodiments, broadcasting of one or more components of the disclosed formulations together prior to blending is required to facilitate the blending process. In particular embodiments, one or more binders, such as PEG-8000, are added and blended until completely dispersed. In particular embodiments, a lubricant, such as sodium caprylate, is added after the binder and blended for approximately 1 to 5 minutes.

Aspects of the disclosed methods include transferring the blend to a standard rotary style Tablet Press (36 Station Stokes 454). Typical rotary style tablet presses consist of upper and lower punches, dies, hopper, feed frame and a die table with appropriate controls and cams to compress an accurate and consistent amount of formulation into a tablet. In some embodiments, the formulation is fed to a hopper. The feed frame delivers the formulation from the hopper to the dies. In some embodiments, the lower punch is set to a certain position in the die to determine the desired fill or tablet weight. As the machine rotates the corresponding upper punch is directed into the die. The method also comprises the press continues its rotation the upper and lower punches travel through pre and final compression stations where compression rollers apply specific amounts of tonnage or pressure forcing the punches together within each die to form a tablet. As the press continues in its rotation the tablet is ejected from the die.

In particular embodiments, tablet samples are evaluated and measured for hardness, weight, and thickness to ensure the tablets meet predetermined and required tablet characteristic during compression. Pharmaceutical tablets are made, usually, to conform or to meet USP dissolution and disintegration specifications.

Tablets are then coated using coating equipment (Thomas Engineering Inc., Hoffman Estates, Ill.). In certain embodiments, the coat is a mixture of water, Kollicoat IR, and PEG. In particular embodiments, tablets are loaded into the coating pan and brought up to temperature and then the pan rotates tumbling the tablets in preparation for coating. A metering pump can be used to deliver the coating solution to air atomizing nozzles. The volume of spray solution and the PSI of the compressed air delivered to the atomizing nozzles can be adjusted depending on the needs of one of ordinary skill in the art. The nozzles are positioned to spray the atomized solution directly on to the tumbling tablets. In some embodiments, temperature controlled air is blown through the tablets as they tumble helping to apply the atomized spray while drying the coating solution onto each tablet. Once the appropriate amount of coating has been applied to the tablets, the tablets are dried for a time and then moved into packaging.

EXAMPLES

1. Example 1. Core Formulation

Tablets according to the embodiments described herein were made as follows. Each batch was made using the following amounts of active pharmaceutical ingredients and excipients. The weight of each active pharmaceutical ingredient and excipient per 24 tablets is also provided (Table 1).

TABLE 1

Tablet Ingredients (full dose)

| Ingredient (g) | 4700-8 24 tabs | 4700-10 24 tabs | 4700-12 24 tabs |
|---|---|---|---|
| $Na_2SO_4$ | 35.5 | 34.6 | 35.5 |
| $MgSO_4$ | 5.4 | 7.8 | 5.4 |
| KCl | 4.5 | 3.7 | 4.5 |
| NaCaprylate | 0.844 | 0.844 | 0.168 |
| PEG-8000 | 1.60 | 1.60 | 2.080 |

Table 2 shows the ingredients contained in the FDA approved comparator products. Tables 3 and 4 show the composition (in mM) of the tablet formulations and comparator products, respectively.

TABLE 2

FDA Approved Prep Ingredients (full dose)

| Ingredient (g) | SUPREP | GoLYTELY 4 L | NuLYTELY 4 L | MoviPrep 2 L |
|---|---|---|---|---|
| PEG | 0 | 236.0 | 420.0 | 200.0 |
| $Na_2SO_4$ | 35.0 | 22.74 | 0 | 15.0 |
| $K_2SO_4$ | 6.26 | 0 | 0 | 0 |
| $MgSO_4$ | 3.2 | 0 | 0 | 0 |
| KCl | 0 | 2.97 | 1.48 | 2.03 |
| NaCl | 0 | 5.86 | 11.2 | 5.38 |
| $NaHCO_3$ | 0 | 6.74 | 5.72 | 0 |
| NaAscorbate | 0 | 0 | 0 | 11.8 |
| NaCaprylate | 0 | 0 | 0 | 0 |
| Ascorbate | 0 | 0 | 0 | 9.4 |
| Malic acid | 0.63 | 0 | 0 | 0 |
| Citric acid | 0.63 | 0 | 0 | 0 |

TABLE 3

Tablet Prep Composition mM (full dose)

| Component (mmol) | 4700-8 24 tabs | 4700-10 24 tabs | 4700-12 24 tabs |
|---|---|---|---|
| $SO_4$ | 295 | 309 | 295 |
| Na | 500 | 493 | 500 |
| K | 60 | 50 | 60 |
| Mg | 45 | 65 | 45 |
| Cl | 60 | 50 | 60 |

TABLE 4

FDA Approved Prep Composition mM (full dose)

| Component (mmol) | SURPEP | GoLYTELY 4 L | NuLYTELY 4 L | MOVIPREP 2 L |
|---|---|---|---|---|
| PEG | 0 | 70.4 | 125.2 | 59.7 |
| $SO_4$ | 308.9 | 160.1 | 0 | 86.1 |
| Na | 492.8 | 500.6 | 259.7 | 225.6 |
| K | 71.8 | 40.0 | 19.8 | 27.2 |
| Mg | 26.6 | 0 | 0 | 0 |
| Cl | 0 | 140.2 | 211.4 | 119.3 |
| $HCO_3$ | 0 | 80.2 | 68.1 | 0 |
| Ascorbate | 0 | 0 | 0 | 114.4 |
| Citrate | 6.3 | 0 | 0 | 0 |
| Malic | 4.7 | 0 | 0 | 0 |

2. Administration of Tablets and Formulations i. Study Parameters

Various tablet formulations were evaluated and compared to FDA approved, marketed preparations (NuLYTELY, SUPREP, MOVIPREP) in an IRB approved protocol following an open label design study at a single site. Depending on the results from each formulation a new formulation was designed and evaluated in a subsequent study, etc. Healthy normal male volunteers 18-50 years of age were recruited. Each formulation or marketed preparation was studied in groups of five volunteers at a time (one cohort). This was usually repeated to give a total of 10 or more volunteers for each formula.

ii. Study Procedures

Study inclusion criteria required that volunteers were male between the ages of 18 and 50 years; were in good health, as judged by a physical examination and review of medical history; and in the investigator's judgment the subject was mentally competent to sign an instrument of informed consent. All study volunteers signed an approved informed consent document. Exclusion criteria were as follows:
1. Subjects known or suspected of having ileus, gastrointestinal obstruction, gastric retention, bowel perforation, colitis, megacolon, or colostomy.
2. Subjects with a history of clinically significant abnormal ECGs or a clinically significant abnormal ECG at the screening visit.
3. Subjects on salt-restricted diets, those with a history or evidence of dehydration, ascites, electrolyte disturbances, renal insufficiency, heart disease or who were taking diuretics or other medications that affect electrolytes.
4. Subjects who had a bowel cleansing procedure within the past month or who took a laxative within the past 5 days (120 hours) before dosing.
5. Subjects who had participated in an investigational clinical, surgical, drug, or device study within the past 90 days.
6. Subjects who had hepatitis B or C or were HIV positive at screening.
7. Subjects who were drug users and/or use (have used) alcohol to excess (more than 1 liter of beer per day or the equivalent amount of any other alcoholic beverage).
8. Subjects who had any ongoing medical problems, including diarrhea, or any subject who was scheduled for surgical procedures or who had a history of clinically significant, hepatic, neurologic, hematologic, endocrine, oncologic, pulmonary, immunologic, psychiatric, cardiovascular disease, or any other condition that, in the opinion of the Investigator, would jeopardize the safety of the subject or impact the validity of the study results.
9. Subjects who were allergic to any preparation components; sodium sulfate, potassium sulfate or magnesium sulfate, citric acid or citrate, malic acid, magnesium citrate, magnesium chloride, sodium or potassium bicarbonate, potassium chloride or polyethylene glycol-3350.
10. Subjects who had experienced severe chronic constipation within the past 3 months.

A screening visit was performed within 28 days before confinement in the clinic where, following the informed consent process, study volunteers provided their medical history and vital signs were obtained. Clinical laboratory tests (including serology), a urine drug screen test (including alcohol), a physical examination and 12-lead ECG were performed.

In general, the tablet ingestion regimen in these studies employed administration of 12 or 14 tablets for a total of two or, in some study groups, three administrations given about 12 hours apart. Marketed preparations were given as split dose following the same schedule as tablets. Beginning on Day −1, groups of five subjects were confined to the site for up to 48 hours, dependent on the dose schedule. Study volunteers were offered a light meal (breakfast or lunch depending upon the regimen assigned) and were given water (in some experiments clear liquids were allowed) thereafter. Urinalysis, urine drug screen, blood chemistry, hematology and coagulation tests were performed and reviewed to assure the volunteers met study entry criteria. A physical examination was also performed.

iii. Administration of Tablets

Beginning at 7 PM, on Day −1, the five study subjects begin taking their 12 or 14 tablets (Dose 1) as quickly as possible along with 16 ounces of water to help swallow the pills. The entire administration (i.e. all 12 or 14 tablets), together with the 16 ounces of water, was expected to be consumed within approximately 20 minutes. Following completion of the first administration, subjects were instructed to drink two (2) additional servings of 16 ounces of water over the next hour at a rate of approximately 8 ounces of water every fifteen minutes. Blood was collected for clinical chemistry, hematology, coagulation, and sulfate within 60 minutes before Dose 1 administration. Blood samples for clinical chemistry and serum sulfate analysis were also collected at interval after the Dose, usually 4 and 6 hours. In later studies, subjects provided an expiratory air sample prior to tablet administration and at 1, 2, 4, and 6 hours after each Dose to test for hydrogen and methane breath gases. Subjects collected all stool and urine voided beginning at approximately from the time of Dose 1 on Day −1 until prior to Dose 2 (the second administration) on Day 1 (Dose 1 Pool).

Beginning at 7 AM, on Day 1, the subjects begin taking their second administration of 12 or 14 tablets (Dose 2) with 16 ounces of water as before. Following completion of Dose 2, subjects consumed two (2) additional servings of exactly 16 ounces of water over the next hour at a rate of approximately 8 ounces of water each fifteen minutes. As before, blood was collected for clinical chemistry, hematology, coagulation, and sulfate within approximately 60 minutes before Dose 2 and after the Dose, usually at 4 and six hours. In addition, (in later studies) subjects provided expiratory air samples prior to Dose 2 and at 1, 2, 4, and 6 hours following the Dose. Subjects also collected all stool and urine voided beginning at approximately from the time of Dose 2 on Day 1 until check-out (Dose 2 Pool). Subjects remained in the clinic for 8 hours after Dose 2, were offered a standard meal, and released after all procedures were completed.

Each bowel movement (BM) that was passed by a subject after each Dose until prior to the start of the next Dose or the end of study was collected in separate labeled containers, one for each bowel movement. The time and weights of each BM were recorded. Stool solids were measured in the last BM that occurred on or before 4, 6, and 8 hours, and in the final BM sample following each Dose using the method of Patel et al., 2009. After the samples were weighed and aliquots obtained for stool solids, all individual BM samples from each Dose were pooled and analyzed for osmolality and electrolytes (sodium, potassium, chloride, bicarbonate, phosphate, magnesium).

Assessments to determine the efficacy of a given formulation included total stool volume (output), percent solids, fecal electrolyte balance, and blood electrolyte results. Beginning with Cohort 7, breath gases were measured as described. Volunteer tolerance to each preparation was monitored and safety was assessed using adverse event data. Descriptive statistics (mean, standard deviation, ranges) were used to compare the data.

3. Results

Cohorts of 5 male volunteers each were studied according to the procedures described above. The protocol identifiers, cohorts, corresponding study subject numbers and formulas tested are shown below in Table 5.

TABLE 5

| Protocol | Cohort: | Prep | Subject #s |
|---|---|---|---|
| 4700-102 | 15 | 4700.8 | 174-178 |
| 4700-102 | 16 | 4700.10 | 179-188 |
| 4600-101 | 1 | SUPREP | 56-60 |
| 800-103 | 1 | SUPREP | 006-010 |
| 800-103 | 2 | SUPREP | 011-015 |
| 4600-101 | 1 | NuLYTELY | 001-005 |
| 4600-101 | 8 | NuLYTELY | 036-040 |
| 4600-101 | 13 | MoviPrep | 061-065 |
| 4600-101 | 16 | MoviPrep | 076-080 |

The intent of these studies was to develop a tablet formulation with similar stool volume output and percent stool solids (surrogates for cleansing) and stool electrolyte balance relative to the FDA approved commercial control preparations.

TABLE 6

| | Control Preparations Mean Stool Output | | |
|---|---|---|---|
| Measure (SD) | SUPREP | NuLYTELY | MOVIPREP |
| N | 15 | 10 | 9 |
| Input (water + prep) | 4547.5 (1048.0) | 4050.0 (898.6) | 4735.6 (817.4) |
| Stool Output | 3386.0 (453.0) | 3343.4 (930.4) | 3031.7 (620.7) |

Table 6 shows the mean stool output results for each of the control preparations and shows the total amount of prep ingested plus any supplemental water from the start of Dose 1 until the end of study and the resulting total stool output. These preparations have been approved by FDA for bowel cleansing for colonoscopy.

Table 7 shows the average of the stool percent solids measured after each dose of approved preparation.

TABLE 7

| | Control Preparations Mean Stool Percent Solids (SD) | | |
|---|---|---|---|
| Formula | SUPREP | NuLYTELY | MOVIPREP |
| N | 15 | 10 | 9 |
| Stool Solids Dose 1 | 5.6 (3.5) | 17.3 (12.0) | 15.3 (10.8) |
| Stool Solids Dose 2 | 2.4 (1.3) | 3.1 (1.8) | 5.4 (4.8) |

As indicated in Table 7, a stool percent solids result less than 5% would be expected to correlate with acceptable colonoscopy cleansing, with 2.4% being the best achievable. Table 8, below, shows the mean stool electrolyte balance results for the three control preparations for sodium, potassium, chloride, magnesium and bicarbonate. For each electrolyte the total amount of electrolyte ingested from Dose 1 and 2 of the prep is shown as "Input". The total electrolyte excreted in the stool following both doses is shown as "Output". The difference between Input and Output is shown as "Gain/Loss" and represents net absorption (Gain) or loss (secretion) of electrolyte from the intestinal tract. As indicated in the table, the three commercial preparations differ with respect to stool electrolyte balance under the conditions of this protocol.

TABLE 8

| | Control Preparations Mean (SD) Stool Electrolyte Balance Results | | |
|---|---|---|---|
| Formula | NuLYTELY (10) | MOVIPREP (9) | SUPREP (15) |
| N | 10 | 9 | 15 |
| Na Input | 259.7 | 362.9 | 492.8 |
| Na Output | 207.9 (63.5) | 340.2 (105.2) | 543.1 (150.0) |
| Na + Balance | 51.9 (63.5) | 22.7 (105.2) | −50.3 (150.0) |
| K Input | 18.8 | 27.2 | 71.8 |
| K Output | 39.0 (14.8) | 74.0 (61.9) | 74.7 (25.0) |
| K + Balance | −19.1 (14.8) | −46.8 (61.9) | −2.3 (25.0) |
| Cl Input | 210.4 | 119.3 | 0.0 |
| Cl Output | 133.8 (46.5) | 75.4 (36.1) | 71.7 (22.1) |
| Cl + Balance | 76.6 (46.5) | 43.9 (36.1) | −71.7 (22.1) |
| Mg Input | 0.0 | 0.0 | 26.6 |
| Mg Output | 5.5 (2.9) | 8.7 (4.3) | 26.6 (8.9) |
| Mg + Balance | −5.5 (2.9) | −8.7 (4.3) | 0.004 (8.9) |
| $HCO_3$ Input | 68.1 | 0.0 | 0.0 |
| $HCO_3$ Output | 64.6 (16.7) | 35.1 (15.3) | 47.0 (13.9) |
| $HCO_3$ + Balance | 3.5 (16.7) | −35.1 (15.3) | −47.0 (13.9) |

For Table 8, a positive number in the Balance row of each indicates a net gain of the particular electrolyte, while a negative number indicates a net loss of electrolyte. All three commercial preparations had individually variable sodium movement which appears to be related to stool volume output, but overall sodium movement was neutral. SUPREP was associated with large chloride losses and NuLYTELY showed large gains. This is due to the absence of chloride in SUPREP and the large quantity of chloride in the NuLYTELY formulation. NuLYTELY also exhibited some potassium loss. Mean results for blood electrolyte and anion gap measurements are shown in Table 9 for the control preparations.

TABLE 9

| | | Control Preparations Mean (SD) Blood Electrolytes | | |
|---|---|---|---|---|
| Analyte (normal range) | Time | SUPREP | NuLYTELY | MOVIPREP |
| N | | 15 [a] | 10 | 10 |
| Na | PreDose 1 | 145.5 (1.7) | 145.0 (2.2) | 147.2 (2.1) |
| (143-152 | 2-4 h post Dose 1 | 146.2 (1.2) | — | 147.5 (1.2) |
| mmol/L) | 2-4 h post Dose 2 | 146.2 (1.6) | 145.3 (2.3) | 146.6 (2.5) |
| K | PreDose 1 | 4.4 (0.3) | 4.4 (0.3) | 4.4 (0.3) |
| (3.7-5.6 | 2-4 h post Dose 1 | 4.7 (0.3) | — | 4.5 (0.3) |
| mmol/L) | 2-4 h post Dose 2 | 4.7 (0.4) | 4.6 (0.5) | 4.7 (0.5) |
| Cl | PreDose 1 | 101.5 (1.6) | 102.8 (1.6) | 102.3 (2.7) |
| (99-108 | 2-4 h post Dose 1 | 102.2 (1.8) | — | 103.7 (2.3) |
| mmol/L) | 2-4 h post Dose 2 | 102.3 (1.8) | 103.1 (1.5) | 103.8 (3.0) |
| Mg | PreDose 1 | 2.1 (0.1) | 2.1 (0.1) | 2.0 (0.1) |
| (1.7-2.6 | 2-4 h post Dose 1 | 2.1 (0.1) | — | 2.0 (0.1) |
| mg/dL) | 2-4 h post Dose 2 | 2.1 (0.1) | 2.1 (0.1) | 2.0 (0.1) |
| $HCO_3$ | PreDose 1 | 28.2 (1.4) | 27.7 (1.4) | 26.6 (1.8) |
| (23-33 | 2-4 h post Dose 1 | 28.3 (1.5) | — | 27.8 (1.8) |
| mmol/L) | 2-4 h post Dose 2 | 27.8 (2.1) | 28.0 (1.3) | 26.5 (2.3) |
| Anion | PreDose 1 | 20.2 (1.2) | 18.9 (1.7) | 20.9 (2.2) |
| Gap | 2-4 h post Dose 1 | 20.3 (1.4) | — | 21.0 (2.2) |
| (3-11 mEq/L) | 2-4 h post Dose 2 | 20.8 (1.5) | 18.8 (2.4) | 21.0 (2.2) |

[a] 15 subjects for PreDose 1, and 2-4 hours post dose 1. 10 Subjects for 2-4 hours post dose 2

Table 10 shows the results of stool output measurements for the tablet formulations.

TABLE 10

Tablet Preparations
Mean Stool Output ml (SD)

| Formula | 8 | 10 | 12 |
|---|---|---|---|
| N | 10 | 9 | 4 |
| Input (water + prep) | 5125.5 (1146.5) | 5002.8 (1387.0) | 4425.8 (652.7) |
| Stool Output | 2632.2 (1146.5) | 2731.3 (423.1) | 2888.5 (306.9) |

Formulas 8, 10, and 12 produced stool output between 2600 ml and about 2900 ml using 24 tablets of the formula. Although the stool output from the tablet formulations was somewhat less than that achieved by the commercial controls, the average percent fecal solids of the lowest fecal solids result measured following each dose of tablets (a measure of colon cleansing) was the same or better, as shown in Table 11.

TABLE 11

Tablet Preparations
Mean (SD) Stool Percent solids

| Formula | 8 | 10 | 12 |
|---|---|---|---|
| N | 10 | 10 | 5 |
| Stool Solids Dose 1 | 3.1 (2.7) | 1.0 (1.4) | 3.6 (2.9) |
| Stool Solids Dose 2 | 1.6 (1.0) | 2.2 (1.3) | 1.6 (0.3) |

Table 12 shows the stool electrolyte balance result for each tablet preparation.

TABLE 12

Tablet Preparations
Mean (SD) Stool Electrolyte Balance Results in mM

| | 8 | 10 | 12 |
|---|---|---|---|
| N | 9 | 9 | 4 |
| Na Input | 504.9 | 493.7 | Pending |
| Na Output | 461.5 | 501.7 | Pending |
|  | (60.7) | (143.5) | Pending |
| NA +Gain/−Loss | 43.4 | −8.0 | Pending |
|  | (60.7) | (143.5) | Pending |
| K Input | 60.4 | 49.6 | Pending |
| K Output | 58.0 | 65.2 | Pending |
|  | (14.1) | (14.3) | Pending |
| K +Gain/−Loss | 2.4 | −15.6 | Pending |
|  | (14.1) | (14.3) | Pending |
| Cl Input | 60.4 | 49.6 | Pending |
| Cl Output | 59.7 | 70.9 | Pending |
|  | (23.7) | (54.8) | Pending |
| Cl +Gain/−Loss | 0.7 | −21.3 | Pending |
|  | (23.7) | (54.8) | Pending |
| Mg Input | 22.4 | 64.8 | Pending |
| Mg Output | Pending | Pending | Pending |
|  | Pending | Pending | Pending |
| Mg +Gain/−Loss | Pending | Pending | Pending |
| HCO$_3$ Input | 0.0 | 0.0 | Pending |
| HCO$_3$ Output | NA | NA | Pending |
|  | NA | NA | Pending |
| HCO$_3$ +Gain/−Loss | NA | NA | Pending |
|  | NA | NA |  |

As shown in Table 12, sodium movement was individually variable (indicated by the large standard deviations). Overall, Formulas 8 and 10 had sodium movements within the sample standard deviation, indicating minimal loss or gain of this electrolyte. For potassium, Formulas 8 and 10 had mean balances within the sample standard deviation with Formula 8 showing the numerically smallest mean balances. With respect to chloride, Formulas 8 showed little or no movement.

Mean blood electrolyte results for the tablet formulations are shown in Table 13, below and reveal no important changes. Anion gap was improved in Formulas 8 and 10.

TABLE 13

Mean (SD) Blood Electrolytes Tablet Preparations

| Analyte (normal range) | Sample Period | 8 | 10 | 12 |
|---|---|---|---|---|
| N |  | 10 | 10 | 4 |
| Na | PreDose 1 | 145.2 (1.2) | 146.5 (1.4) | 147.3 (0.5) |
| (143-152 | 4 h Dose 1 | 144.8 (1.8) | 146.1 (1.4) | 147.8 (0.8) |
| mmol/L) | 4 h Dose 2 | 143.9 (1.3) | 145.9 (1.4) | 146.8 (1.5) |
| K | PreDose 1 | 4.3 (0.3) | 4.3 (0.1) | 4.3 (0.2) |
| (3.7-5.6 | 4 h Dose 1 | 4.3 (0.2) | 4.3 (0.3) | 4.7 (0.2) |
| mmol/L) | 4 h Dose 2 | 4.6 (0.3) | 4.6 (0.3) | 5.0 (0.4) |
| Cl | PreDose 1 | 102.0 (1.5) | 101.6 (1.7) | 101.0 (0.8) |
| (99-108 | 4 h Dose 1 | 101.7 (2.5) | 100.6 (2.5) | 102.5 (1.1) |
| mmol/L) | 4 h Dose 2 | 101.0 (1.9) | 101.0 (1.8) | 103.3 (1.3) |
| Mg | PreDose 1 | 2.0 (0.1) | 2.1 (0.1) | 2.1 (0.1) |
| (1.7-2.6 | 4 h Dose 1 | 2.2 (0.1) | 2.2 (0.2) | 2.4 (0.1) |
| mg/dL) | 4 h Dose 2 | 2.2 (0.1) | 2.3 (0.2) | 2.5 (0.1) |
| HCO$_3$ | PreDose 1 | 27.3 (1.6) | 27.6 (2.4) | 28.0 (0.0) |
| (23-33 | 4 h Dose 1 | 26.7 (1.3) | 27.6 (2.5) | 28.5 (0.5) |
| mmol/L) | 4 h Dose 2 | 26.0 (1.5) | 28.0 (1.0) | 28.0 (2.5) |
| Anion Gap | PreDose 1 | 20.2 (2.2) | 21.6 (2.8) | 22.7 (0.7) |
| (3-11 | 4 h Dose 1 | 20.7 (2.0) | 22.2 (3.5) | 21.4 (1.3) |
| mEq/L) | 4 h Dose 2 | 21.5 (1.9) | 21.5 (0.9) | 20.5 (2.9) |

A tablet formulation is considered to be a more convenient dose form that will encourage patient compliance than ingestion of salty tasting liquids. Tablet formulas were evaluated for performance with respect to the bowel cleansing surrogate markers of stool output volume and percent solids in diarrheal stools. The stools were also evaluated to determine the ability of the formulation to provide neutral movement of electrolytes between the body and the formulation. The goal of the project was to attain stool output and clarity as close to the FDA approved commercial products as possible while maintaining minimal movement of electrolytes.

All of the formulas tested used a total of 24 tablets administered in two 12 tablet doses. None of the formulations adversely affected serum electrolytes. Most were able to produce stool volumes and percent solids similar to that achieved by the FDA approved commercial products. Although the stool volumes produced by the tablet formulations were slightly lower than the commercial preparations, the equivalence or superiority of the stool percent solids measurements (a measure of colon cleansing) indicates that the commercial preparations may produce unnecessary output.

Formulas 8, 10, and 12 reduced the sodium content (by reducing sodium sulfate) and provided compensating sulfate by adding magnesium sulfate, which also provided necessary magnesium to the formulation. Formulas 8, 10, and 12 used potassium chloride as a source of those electrolytes and are very similar.

Formulas 8, 10, and 12 provide acceptable stool output, percent solids measurements and minimal absorption/secretion of electrolytes. All show no propensity to significantly alter blood electrolytes and improve anion gap over SUPREP. All of these formulas are eligible for further study in colonoscopy patients.

What is claimed:

1. A solid oral formulation for cleansing a colon of a subject; the formulation comprising about 35.5 grams of sodium sulfate, about 5.4 grams of magnesium sulfate, and about 4.5 grams of potassium chloride.

2. The solid oral dosage form of claim 1 further comprising polyethylene gly-col.

3. The solid oral dosage form of claim 1 further comprising one or more water-soluble excipients.

4. The solid oral dosage form of claim 3, wherein the one or more water-solu-ble excipients comprises sodium caprylate.

5. The solid oral dosage form of claim 1, wherein the solid oral dosage form further comprises polyethylene glycol and the polyethylene glycol is PEG-8000.

6. The solid oral dosage form of claim 1 is divided into a first dose and a second dose.

7. The solid oral dosage form of claim 1, wherein the solid oral dosage form is a tablet.

* * * * *